United States Patent
Assa et al.

(10) Patent No.: US 7,951,139 B2
(45) Date of Patent: May 31, 2011

(54) LASER SURGICAL APPARATUS

(75) Inventors: Shlomo Assa, Valley Center, CA (US); Steven Jerome Meyer, San Diego, CA (US); John F. Stine, Murrieta, CA (US)

(73) Assignee: Inlight Corporation, San Diego, CA (US)

( * ) Notice: Subject to any disclaimer, the term of this patent is extended or adjusted under 35 U.S.C. 154(b) by 34 days.

(21) Appl. No.: 12/016,871

(22) Filed: Jan. 18, 2008

(65) Prior Publication Data

US 2009/0187176 A1 Jul. 23, 2009

(51) Int. Cl.
*A61B 18/18* (2006.01)

(52) U.S. Cl. .............................. 606/19; 606/11; 606/13

(58) Field of Classification Search ................ 606/9, 13, 606/17, 18, 19
See application file for complete search history.

(56) References Cited

U.S. PATENT DOCUMENTS

| | | | |
|---|---|---|---|
| 3,528,424 A * | 9/1970 | Ayres | 606/19 |
| 3,865,113 A | 2/1975 | Sharon et al. | |
| 3,913,582 A | 10/1975 | Sharon | |
| 4,228,341 A | 10/1980 | Zandberg | |
| 4,517,974 A | 5/1985 | Tanner | |
| 4,597,380 A | 7/1986 | Raif et al. | |
| 4,623,229 A * | 11/1986 | Galan | 359/845 |
| 5,074,861 A | 12/1991 | Schneider et al. | |
| 5,242,438 A | 9/1993 | Saadatmanesh et al. | |
| 5,336,217 A | 8/1994 | Buys et al. | |
| 5,397,327 A * | 3/1995 | Koop et al. | 606/17 |
| 5,454,808 A * | 10/1995 | Koop et al. | 606/17 |
| 5,814,042 A | 9/1998 | Zair | |
| 5,906,609 A | 5/1999 | Assa et al. | |
| 5,938,657 A | 8/1999 | Assa et al. | |
| 6,117,129 A * | 9/2000 | Mukai | 606/10 |
| 6,156,030 A | 12/2000 | Neev | |
| 6,383,177 B1 | 5/2002 | Balle et al. | |
| 6,454,763 B1 | 9/2002 | Motter et al. | |
| 6,595,987 B1 | 7/2003 | Negus et al. | |
| 6,704,959 B2 * | 3/2004 | Schuerch | 5/648 |
| 6,840,934 B2 | 1/2005 | Enomoto | |
| 7,621,637 B2 * | 11/2009 | Rathjen et al. | 351/221 |
| 2001/0016732 A1 * | 8/2001 | Hobart et al. | 606/2 |
| 2002/0016587 A1 * | 2/2002 | Furumoto | 606/7 |
| 2002/0161359 A1 * | 10/2002 | Yamamoto | 606/19 |

(Continued)

OTHER PUBLICATIONS

Young, Lee W., Authorized Officer, Patent Cooperation Treaty, PCT Application No. PCT/IL09/00058, filed Jan. 15, 2009, International Search Report, mailed Jun. 2, 2009, published by WIPO, 8 pages.

*Primary Examiner* — Henry M Johnson, III
*Assistant Examiner* — Jeffrey B Lipitz
(74) *Attorney, Agent, or Firm* — Fish & Richardson P.C.

(57) ABSTRACT

A laser surgical apparatus for performing treatment by irradiating a part to be treated by a laser beam is disclosed. This apparatus includes a laser source which emits the treatment laser beam; a multi-articulated arm for delivering the treatment laser beam emitted from the laser source, the arm including a plurality of light delivery pipes, a joint part for jointing the light delivery pipes, the joint part being rotatable with respect to at least one of the pipes jointed by the joint part, a reflection mirror disposed in the joint part; and a surgical instrument is connected to an end of the arm and used for irradiating the treatment laser beam delivered therein through the arm to the treatment part.

19 Claims, 5 Drawing Sheets

U.S. PATENT DOCUMENTS

| | | |
|---|---|---|
| 2003/0028181 A1* | 2/2003 | Enomoto ........................ 606/19 |
| 2003/0028967 A1* | 2/2003 | Schuerch ......................... 5/621 |
| 2003/0191455 A1* | 10/2003 | Sanchez et al. .................... 606/1 |
| 2004/0059320 A1 | 3/2004 | Telandro et al. |
| 2004/0097910 A1* | 5/2004 | Brugger et al. ................. 606/10 |
| 2004/0137408 A1 | 7/2004 | Embert et al. |
| 2004/0259053 A1 | 12/2004 | Bekov et al. |
| 2004/0262866 A1* | 12/2004 | Kraus ........................ 280/47.34 |
| 2005/0197655 A1 | 9/2005 | Telfair et al. |
| 2006/0095096 A1 | 5/2006 | DeBenedictis et al. |
| 2006/0119743 A1 | 6/2006 | Lin |
| 2007/0016178 A1* | 1/2007 | Vaynberg et al. ............... 606/19 |
| 2007/0106128 A1 | 5/2007 | Lavallee |
| 2007/0112342 A1 | 5/2007 | Pearson et al. |
| 2008/0015553 A1 | 1/2008 | Zacharias |
| 2010/0049175 A1* | 2/2010 | Rathjen et al. .................... 606/5 |

* cited by examiner

LASER SURGICAL APPARATUS

CROSS-REFERENCE TO RELATED APPLICATIONS

This application is related to U.S. patent application Ser. No. 12/016,851, entitled LASER SURGICAL METHODS, to inventors Shlomo Assa and Steve J. Meyer, which application was filed on the same day as the present application; and this application is related to U.S. patent application Ser. No. 12/016,923, entitled DISPOSABLE HAND PIECE FOR DENTAL SURGICAL LASER, to inventors Shlomo Assa, Steve J. Meyer, Julie Assa and Gordon J. Foote, which application was filed on the same day as the present application. The disclosures of the above two applications are incorporated herein by reference in their entirety.

BACKGROUND

This specification relates to a laser surgical apparatus having a multi-articulated arm and different types of surgical instruments to be used in surgery on both soft and hard tissue.

There have been known laser surgical apparatus for performing treatment by irradiating a part to be treated by a laser beam. For instance, a laser treatment apparatus which emits a carbon dioxide laser beam having infrared wavelengths has been used in plastic surgery treatments for removing wrinkles, birthmarks, etc. of patients.

In an apparatus of this type, the treatment beam emitted from a laser source is guided through a multi-articulated arm to a hand-piece mounted on an end of the arm and emerges therefrom to irradiate a treatment part. The arm is provided with a plurality of light delivery pipes and joints each jointing the pipes. In each joint, a reflection mirror is disposed. An operator manipulates the arm to position or put the hand-piece onto a target treatment part.

Sharon (U.S. Pat. No. 3,913,582) patented an apparatus for conducting a laser beam from a laser, through an articulated arm, to an output device, said apparatus being constructed so that the output device is easily maneuvered. In one embodiment, a beam from a laser mounted on an optical bench is directed to a first mirror that reflects the beam upward along the axis of a vertical shaft. At the top of the shaft, a second mirror, mounted on a conical bearing and rotatable about the axis of the vertical shaft, reflects the laser beam along the axis of a horizontal sleeve to a third mirror that is mounted on a sleeve bearing so that it is rotatable about the horizontal axis. In like fashion, the beam from the third mirror is successively incident on fourth, fifth, sixth, seventh, and eighth mirrors all of which are rotatable about the axis of the shaft down which the incident beam propagates. Finally, the beam from the eighth mirror enters the output device. The second through eighth mirrors are all mounted in the articulated arm and are interconnected by sleeve bearings and, in some cases, hollow tubes. The arm is supported by a counterbalancing system that is connected to the arm at a point between the third and fourth mirrors.

If treatment needs to be performed on a wide range, for instance, the arm may not be long enough to reach a target treatment part. In this case, the operator needs to move a main unit of the apparatus until the hand-piece can reach the treatment part. This work would be troublesome to the operator and cause a delay in treatment. If a fixed total length of the arm is made too long to solve the above problem, it would be hard to handle.

Enomoto (U.S. Pat. No. 6,840,934) patented a laser treatment apparatus that can extend the treatment reach distance by having the light tubes be extended in length thus allowing the handpiece to reach further away from the apparatus without the need to move the whole unit. At the end of the articulated arm, and connected mechanically to the end of the articulated arm, the laser beam will be guided to a surgical instrument that allows use of the radiation in the laser treatment.

Sharon et al. (U.S. Pat. No. 3,865,113) patented a plurality of surgical scalpels that are used in much different surgical treatment. These scalpels are with fixed optics and they are designed for a free hand surgical treatment.

Zandberg (U.S. Pat. No. 4,228,341) patented a mechanical control apparatus to enable one to manipulate a focused beam in the field of view of a surgical microscope to enable the surgical treatment to be performed using the microscope. In that invention, the mechanical attachment that is mounted mechanically onto the surgical microscope has a mechanical ball mounted drive that tilts a reflecting mirror that causes the manipulation of the laser beam. According with that invention, and as the existing practice, the use of a laser apparatus with a surgical microscope will require the use of an additional instrument, such as the said device.

Similarly, Raif et al. (U.S. Pat. No. 4,597,380) patented an endoscopic attachment to a surgical laser. The attachment is to be used with a surgical laser producing a working laser beam. The coupling device includes a pivotable reflector in the path of the laser beam for reflecting it through the endoscopic tube to the working area at the front end of the tube, and a manipulatable joystick connected to the reflector for manipulating the laser beam to direct it through the endoscopic tube to selected positions in the working area at the front end of the tube. Again, according with that invention, and as existing practice, the use of a laser apparatus with a surgical endoscope will require the use of an additional instrument, such as in that invention.

Zair (U.S. Pat. No. 5,814,042) patented an apparatus for applying a laser beam to a working surface, by displacing the laser beam to trace a plurality of circular scans over the working surface; and continuously varying the diameters of the circular scans at a rate to produce a substantially homogenous distribution of the laser energy over the working surface. According to that invention, an external instrument is connected to the end of the arm, that instrument is electrically powered, using scanning mirrors that deflect the laser beam in a particular circular pattern. Similarly, Assa et at. (U.S. Pat. No. 5,906,609 and U.S. Pat. No. 5,938,657) patented a method and apparatuses to deliver focused laser energy to selected area. The method and device have means to focus a laser beam and means to move the laser beam in both X and Y directions to be directed to a selected area within the marked outline. These methods are currently used in many different applications in the cosmetic surgery field. Again, this attachment is connected to the end of the said articulated arm.

Additionally, articulated arm beam delivery is mechanically sensitive to alignment. The system tends from time to time to become misaligned, at which time the system becomes unusable, until a service technician can repair the system by realigning all the joints.

SUMMARY

This specification describes technologies relating to a laser surgical apparatus having a multi-articulated arm and different types of surgical instruments to be used in surgery on both soft and hard tissue.

In general, one or more aspects of the subject matter described in this specification can be embodied in apparatus and systems for laser surgery that include a multi-articulated arm and are capable of irradiating a treatment radiation while simplifying the use of the energy, and enabling the unit to be more compact and fit in the treatment procedure more effectively. A laser treatment apparatus for performing treatment by irradiating a treatment part with a laser beam for treatment can include: (a) a laser source which emits the treatment laser beam; (b) a dual axis mirrors scanner for translating the laser beam in two axes; (c) a multi-articulated arm for delivering the treatment laser beam emitted from the laser source, the arm including: a plurality of light delivery pipes, joint part for jointing the light delivery pipes, the joint part being rotatable with respect to at least one of the pipes jointed by the joint part, a reflection mirror disposed in the joint part; (d) an imaging optic system that is assembled in the articulated arm components that is designed to image and deliver the treatment laser emission; (e) an air spring device for counterbalancing the system gravity while in use; and (f) a hand-piece connected to an end of the arm and used for irradiating the treatment laser beam delivered therein through the arm to the treatment part.

Particular embodiments of the subject matter described in this specification can be implemented to realize one or more of the following advantages. The sensitivity of the laser surgical systems and apparatus to misalignment can be reduced. Moreover, the process of aligning the laser surgical apparatus can be made easier and can be required less often, resulting in less down time for the medical personnel.

The details of one or more embodiments of the subject matter described in this specification are set forth in the accompanying drawings and the description below. Other features, aspects, and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
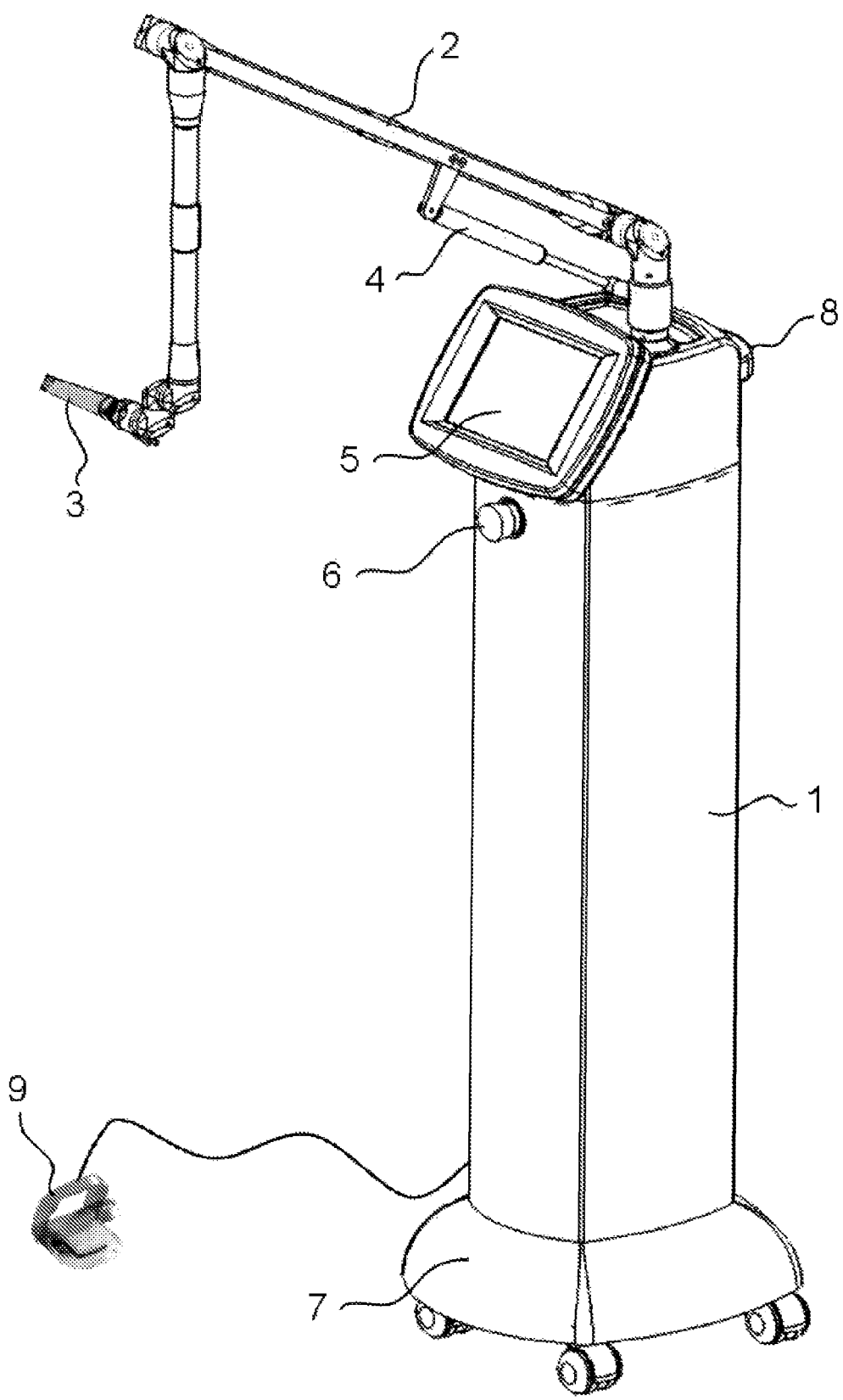
FIG. 1 is a schematic perspective view of a laser surgical apparatus in an embodiment according to the present invention.

FIG. 1 is a schematic perspective view of the laser surgical apparatus, including a main apparatus cabinet 1, the unit resting on a wheel base 7, and handle 8, to move the unit and position it in place. Programming the apparatus operation parameters is done by using LCD touch screen 5, and an emergency stop switch 6 is also provided. An articulate arm beam delivery 2 is counterbalanced with an air spring device 4, and at the end of the arm there is an operating hand piece 3. Activating the laser by depressing a footswitch 9 will emit the treating laser.

Figure 2:
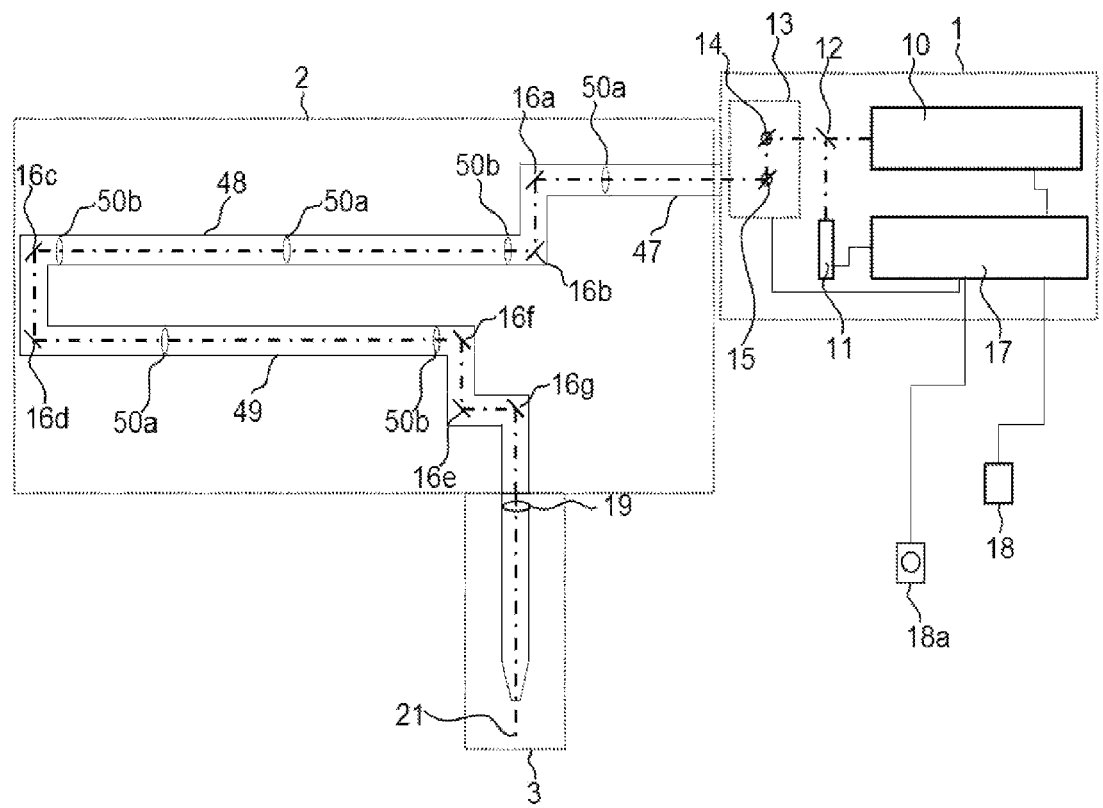
FIG. 2 is a schematic structural view of an optical system and a control system.

FIG. 2 is a schematic structural view of an optical system and a control system of the apparatus in detail. Within main apparatus cabinet 1 there are arranged a laser source 10 to generate treatment, a laser source 11 to generating a visible aiming beam, a beam combining optical window 12, an optical mirror scanner assembly 13, including an X-axis scanner mirror 14 and Y-axis scanner mirror 15, and a control module 17 to execute control of each part of the apparatus, and others. A controlling footswitch 18 generates a trigger signal to start laser irradiation. The beam combing window 12 has particular properties that allow the light from the treatment laser 10 to pass through while it allows reflecting the light from the visible aiming beam 11, which brings the treatment beam and the aiming beam into coaxial relation.

Scanner assembly 13 internally provided with driven mirrors 14 and 15 for causing each laser beam to deflect a part in X- and Y-directions, at a magnitude that is commanded by the apparatus program via the control module 17. The succession of commands for the scanner motor in both X or Y direction will cause both laser beams to deflect and scan.

The control module 17 can generate a two axis scanning command from a pre-programmed selection of shapes and sizes. The laser treatment beam can be scanned in two axes in intermittent steps by the motorized mirror scanners 14, 15. The laser treatment beam can be scanned in two axes in continuous steps by the motorized mirror scanners 14, 15. Moreover, the laser beam can be imaged through the optical relay system, which is arranged inside the articulated arm 2, the laser beam can be focused on a spot, and the focused spot can move in two axes in intermittent steps in a surgery plane.

Figure 5:
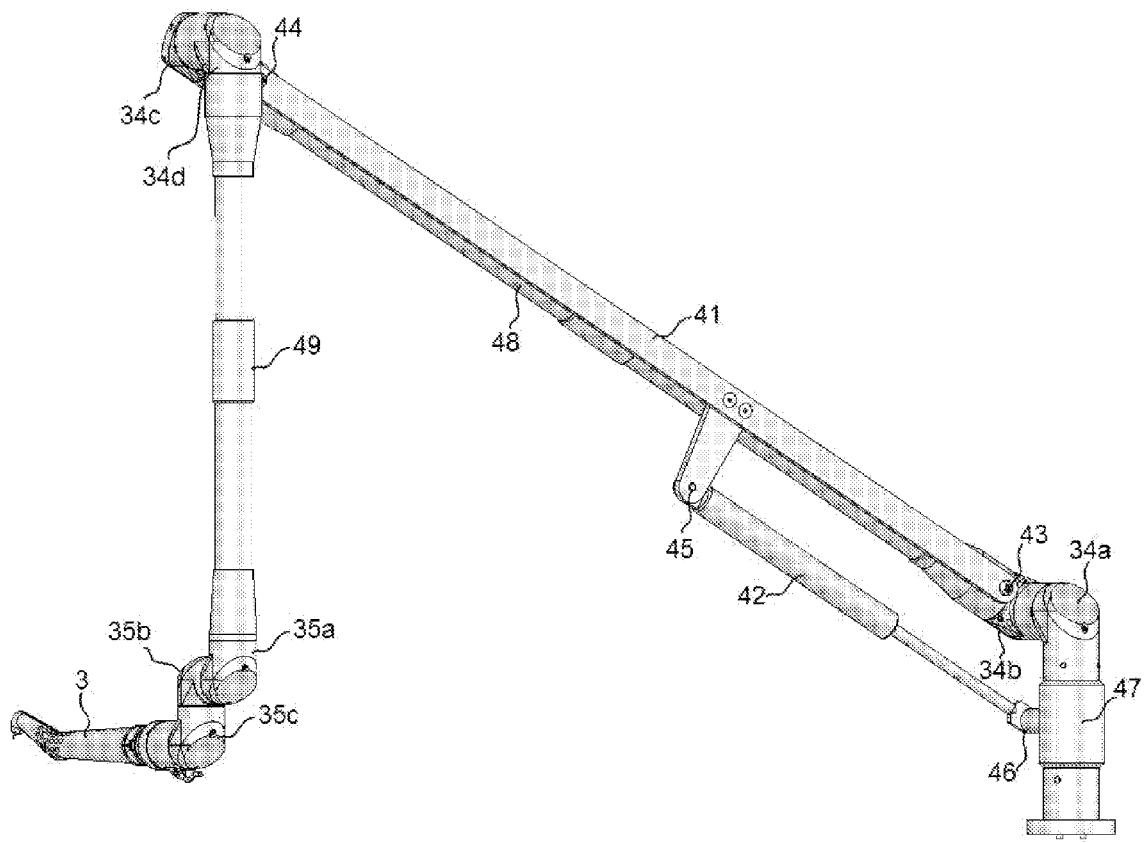
FIG. 5 is a schematic perspective view of the articulated beam delivery system assembly.

FIG. 5 is a schematic perspective view of the articulated beam delivery system assembly. The arm 2 includes a main bearing support 47 extending upward from the top of the main unit 1 and light delivery pipe assemblies 48 and 49 which are constructed to be fixed in length. The main bearing 47 and the light delivery pipe assembly 48 are jointed by joints 34a and 34b which have therein mirrors 16a and 16b respectively (FIG. 2). The pipe assemblies 48 and 49 are similarly jointed by joints 34c and 34d which have therein mirrors 16c and 16d respectively. The joint 34b is rotatable with respect to the main bearing 47; the joint 34a is rotatable with respect to pipe 48. The joint 34c is rotatable with respect to the light delivery pipe assembly 49, and the joint 34d is rotatable with respect to the joint 34c. It is to be noted that an intermediate pipe may additionally be provided between the joints 34c and 34d. In this case, the joint 34d is brought in rotatable relation to pipe 49. The above configuration enables an operator to freely move the arm 2 by holding the hand-piece unit 3 by hand.

In the joints 35a, 35b and 35c, mirrors 16f, 16e and 16g are arranged respectively, which direct each laser beam delivered through the arm 2 (the light delivery pipe assemblies 48, 49, and others) to the hand-piece unit 3. These joints 35a, 35b and 35c enable free movement of the hand-piece unit 3 with respect to the arm 2. The hand-piece unit 3 is internally provided with a condensing lens 19 for converging each laser beam delivered into the unit 3 at a predetermined distance to working plane 21.

Parallel to pipe assembly 48, a support arm 41 is attached to both ends of pipe assembly 48 using screws 43 and 44 respectively. This assembly insures that any balancing load will be transferred to the support arm 41 and will prevent any undesired mechanical deflection to pipe assembly 48.

An air spring device 42, which has the particular properties to be able to generate constant spring force along it's axis, is configured to counterbalance the gravitational weight of the entire articulated arm delivery system. The air spring device 42 can be connected to the support arm 41 using screw 45, and to the main bearing 47 using screw 46. This makes it possible to prevent the weight of the arm 2 from leaning to the hand-piece unit 3 side, so that the hand-piece unit 3 can be prevented from bumping against a floor of an operating room, the main unit 1, or other things. Furthermore, the operability of the arm 2 can be enhanced. In addition, counterbalancing the weight of the system will enable the user to achieve larger degrees of freedom, leading to increased functionality and precision.

It is important to note, that the prior art is based on a counterweight balancing way, in contrast, the use of an air spring device which is part of this invention increases the functionality and capabilities by reducing overall inertia, and making the unit more compact.

Figure 6:
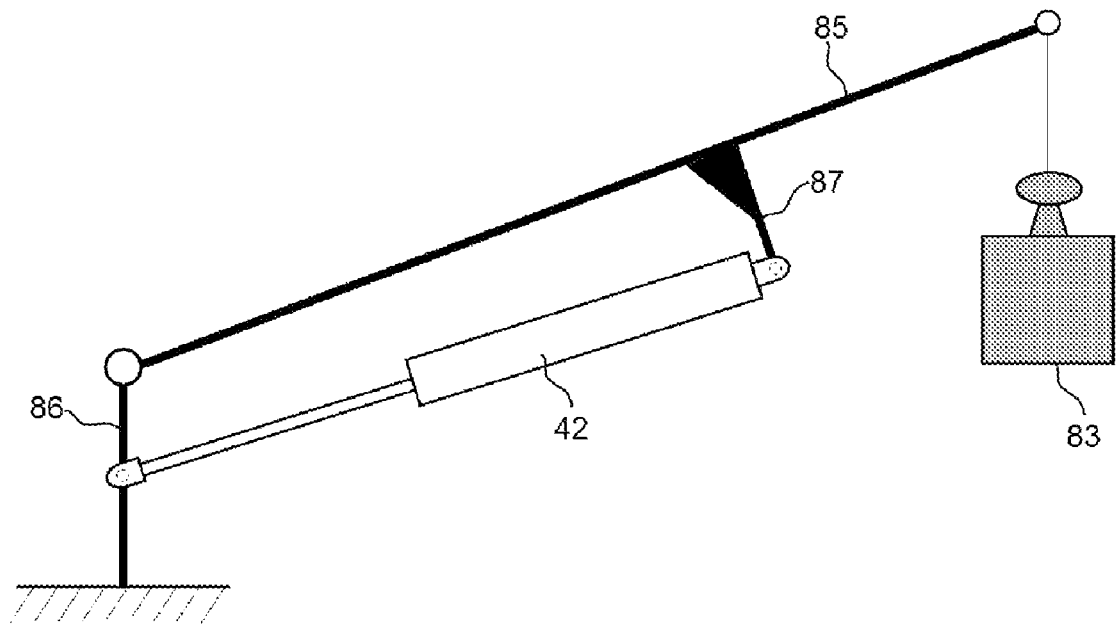
FIG. 6 is a schematic simplified layout of the air spring device counterbalancing the articulated arm gravity.

FIG. 6 is a schematic simplified layout of the air spring device counterbalancing the articulated arm gravity. The gravity weight of the arm is represented by weight 83. The air spring device is constructed in a way that it creates a fixed reaction force that depends on the air spring size and the gas filling pressure. These type of springs are commonly used in many application were load carrying assistance is needed, such as automotive doors. The air spring device is mounted at a distance 86 from one pivot and a distance 87 from the main pipe assembly 85. The mounting distances 86 and 87 are particular specified along with the system weight and the air spring device reaction force to create balancing forces with the spring reaction being slightly higher in reaction, which will always force the articulated arm upwards, away from crashing to the flour. For example, the unit can be 38 inches tall, the main bearing 47 can then rise 6 inches above, the light pipe 48 can be 23 inches long while light tube 49 can be 12 inches long.

The air spring device 42 can be arranged with adjustable compressed air pressure. The air spring device 42 can be filled with compressed gas that is not compressed air. The air spring device 42 can be filled with compressed gas comprising Nitrogen. The air spring device 42 can be a mechanical telescopic spring device.

Figure 7:
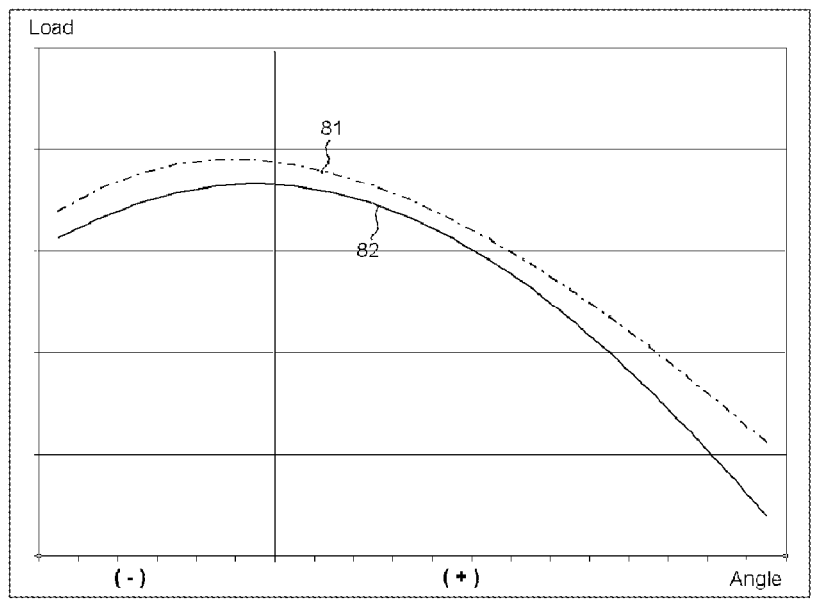
FIG. 7 is a graph diagram of the gravity load of the articulated arm and the air spring device counterbalance reaction.

FIG. 7 is a graph diagram of the gravity load of the articulated arm and the air spring device counterbalance reaction. According to this invention, an optical imaging system is assembled into the articulated arm, to enable the scanned laser beams to be imaged properly to the handpiece 3 at the end of the articulated arm.

FIG. 2 shows the placement of the optical components 50*a* and 50*b* in three groups, with the functional description to follow.

Figure 3:
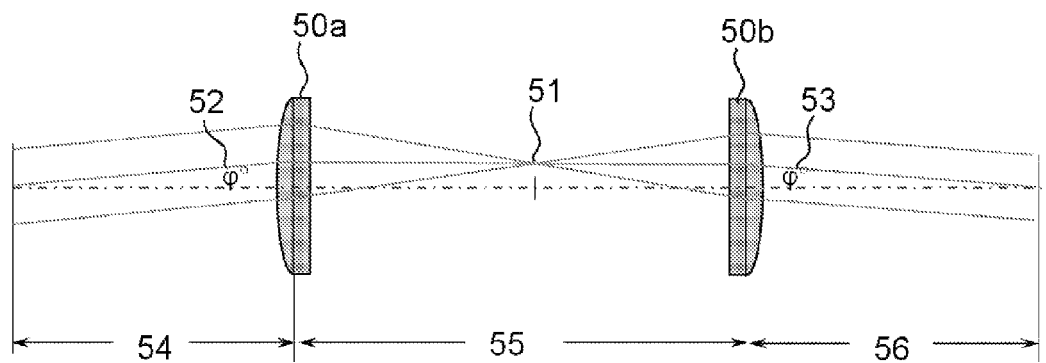
FIG. 3 is a schematic view of single stage relay optics.

FIG. 3 is a schematic view of single stage relay optics. This relay system that is part of this invention is designed to translate an angular scan angle through a distance. Lens 50*a* which is a positive lens, Plano-Convex or Convex-Convex is placed at a distance 54 that is equal to the focal distance, f50*a*, of lens 50*a*. At distance 54 the angular tilt of the beam 52 starts. Lens 50*b* is of the same nature as lens 50*a* but with either identical or different focal distance, f50*b*, is placed at a distance 55 from lens 50*a*. Distance 55 is equal to sum of the focal distance of lens 50*a* plus lens 50*b*, as shown: f50*a*+f50*b*=distance 55.

Since both lenses are positive lenses, the laser beams will be focused to a common focus 51 at the distance between the 2 lenses. At a distance 56 behind lens 50*b* the laser beams are collimated and intersecting the main axis at the center line of the optical system with a relay angle 53.

In some embodiments, the lenses 50*a* and 50*b* are identical in properties, and the focal distance is equal to f=127 mm, and the focused laser spot 51 appears at the half distance 55, and the angle 52 will be equal to the angle 53, and the overall length that the laser beams travel will equal 4×f50*a*=508 mm. The net result of the relay set is that the laser propagated 4×f distance and the scan angle is imaged to the end of that distance.

Three sets of the relay lenses are attached in the articulated arm such that the end of the first system is coincident with the beginning of the second system, and the end of the second system coincident with the beginning of the third system. At the end of the three sets, the lasers have propagated 3×4×f=1524 mm in distance, and the scanned angle is at center line of the optical system as shown in FIG. 3 for the individual set of relay optics.

Figure 4:
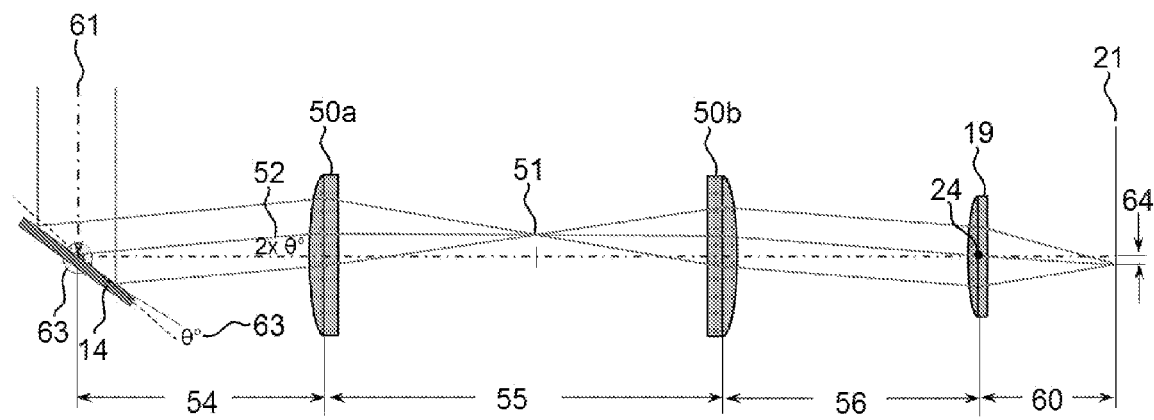
FIG. 4 is a schematic view of the scanning mirror layout with the single stage relay optics and the final focusing optic.

FIG. 4 is a schematic view of the scanning mirror layout with the single stage relay optics and the final focusing optics. In this view only one set of relay optics is used to simplify the detailed description of this invention. The motorized scanner mirror 14 is placed at a distance 54 away from lens 50*a*. The physical distance between the scanner mirror and the first relay optics is shown in FIG. 2. The scanner mirror 14 is driven by an electronic motor 63. The deflection angle for the mirror 14, which is controlled by the control module 17, is equal to half of the laser beam scanned angle 52. This angle is relayed to the other end of the optical set 24, where at a distance 56, the final focusing lens 19 of the system is placed. This lens is part of the handpiece. When the scanner mirrors 14 and 15 are commanded to tilt the laser beam in either X axis or Y axis or a combination of both, the focused spot of the treatment laser will be shifted 64 in X or Y axis or both axis, at the working plane 21 (both FIG. 2 and FIG. 4) that is at a distance 60 that is equal to the focal distance of lens 19.

In some implementations, the system shown in FIG. 2 has three sets of relay optics with translating the scanned angles a distance of approximate 1524 mm away from the scanners. A significant advantage here is that the optical mirror scanner assembly 13, which can often be large and cumbersome and thus obstruct the ability of the user to use the system effectively with great precision, is part of the main unit cabinet 1, and the optical system transfers the scan angle as part of the articulated arm without significant increase in size or weight to the system. This invention enables efficient and unobstructed use of the focused beam with two axis scanners. In addition, the is no need for any electric wiring in close proximity to the treatment since the electronic motors are part of the cabinet 1 and the scanned angle is imaged the distance of the articulated arm by the relay optics.

In some implementations, a manual pointing device such a Personal Computer Mouse 18*a* (FIG. 2) is connected to the main cabinet 1, and is used to enter deflection direction and magnitude, as if the user is using a joystick. This can significantly simplify many surgical procedures. The reason is that for any surgical procedure the physician will use a surgical instrument such as Microscope or Endoscope. It is the prior art common practice that for each surgical tool the physician will connect an adapter that will align the laser beam into the instrument and via a mean to maneuver the laser beam the physician will be able to aim the laser at the proper treatment area. With the present invention, a unique adapter need not be used for each and every surgical tool, since the ability to steer the laser beam and thus align it to the proper area exists in the configuration independent of any unique adapter.

A major drawback to surgical instruments that comprises of an articulated arm beam delivery is that in many instances the reliability of the beam delivery is poor. The main reason for that is that the system is very sensitive to mirror alignment, and any slight change in the mirror position due to mechanical stresses, material bending or loosening of screws will cause the laser beam to become misaligned and that will reduce the functionality until the unit can be repaired by re-aligning it. It is a difficult task to perform in the field which furthermore make this situation extremely undesired. Thus, it is desired to increase the articulated arm beam delivery reliability by making the system less susceptible to misalignment.

Figure 8:
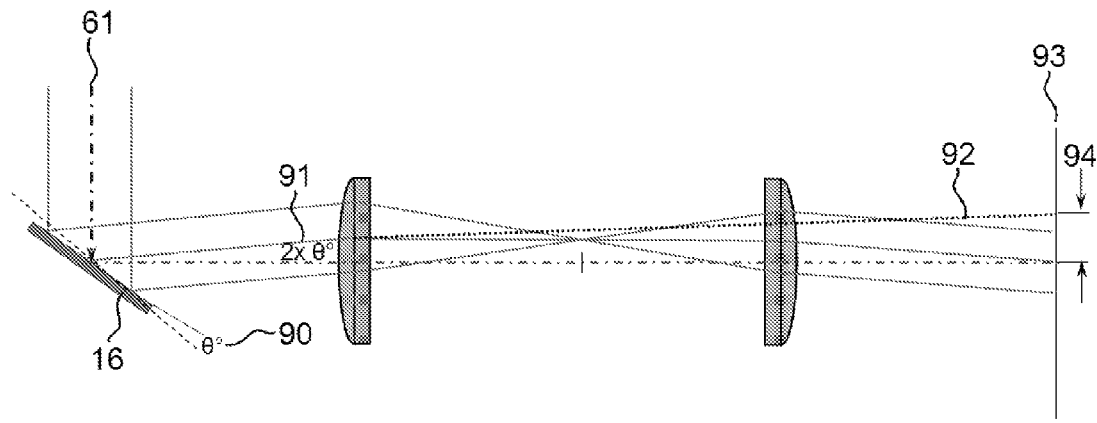
FIG. 8 is a schematic view of mirror misalignment effect on the laser beam propagation.

FIG. 8 is a schematic view of mirror misalignment effect on the laser beam propagation. A mirror 16 can be assembled in any of the rotating joints 35. An angular misalignment movement 90 of the mirror will reflect the laser beam 91 away from the system center line. The angle 91 is twice as large as the angle 90 of the mirror misalignment. This misalignment will cause the laser beam to propagate along 92, away from the center line of the system, accumulating a total misalignment distance 94 at a distance equivalent to the relay lens set. According to the details of this invention, the relay lens optic system will image the angular misalignment and will re-center the beam back around the centerline with no accumulated misaligned distance. The use of relay optics that is part of this invention reduces the sensitivity to misalignment by factor of 8 times in average making the system much more durable, more reliable and less sensitive to any mechanical external changes. Another useful advantage for this approach is that the reduction of sensitivity to misalignment makes the assembly process simpler, faster and less costly.

Figure 9:
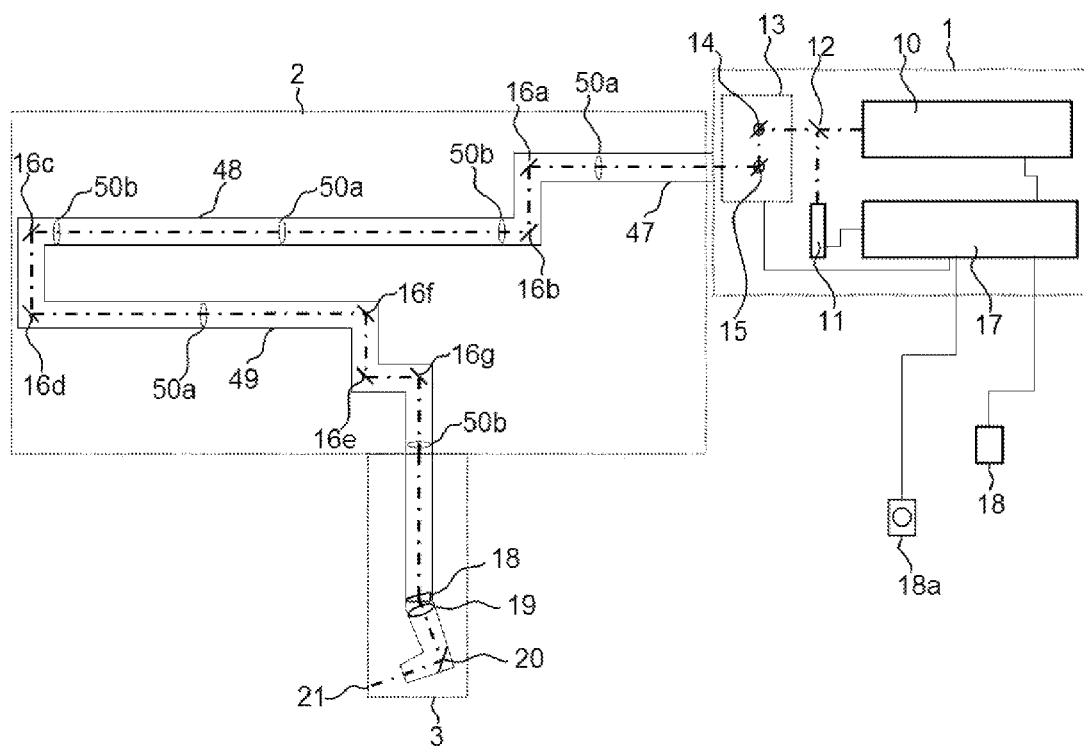
FIG. 9 is a schematic structural view of an optical system and a control system.

FIG. 9 is a schematic structural view of an optical system and a control system as can be used in additional implementations, which can be optimized for use in the field of dental surgery. Handpiece 3 can be a disposable inexpensive part that is made of plastic that is designed to be disposed at the end of the usage, eliminating the need for a costly sterilization of the optical and mechanical assemblies. An optical wedge 18 bends the laser beam at a particular designed angle, and the hand piece can be easily aimed at the oral cavity parts that need the treatment. The final focusing lens 19 and a thin metal reflector 20 focuses and reflects the beam at 90° towards the treatment plane 21. The scanning mirrors image point is exactly at the center of lens 20, and that keeps the hand piece geometry to a small tapered cylinder that does not obstruct the access to the oral cavity.

The optical wedge 18 can bend the laser beam between five to thirty five degrees, and the final focusing lens 19 can be such that the image of the scanning pivot point is in the center of the lens or in a close proximity to the center of the lens. Moreover, a plastic disposable hand piece 3 can be configured for use inside a human oral cavity.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a computer-readable medium. The computer-readable medium can be a machine-readable storage device, a machine-readable storage substrate, a memory device, or a combination of one or more of them.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Thus, particular embodiments of the invention have been described, but other embodiments are within the scope of the following claims.

What is claimed is:

1. A laser surgical apparatus for performing treatment by irradiating a part to be treated by a treatment laser beam, the apparatus comprising:
   a main enclosure including a treatment laser, a visible aiming laser, motorized mirror scanners, and a control device to control the motorized mirror scanners;
   an articulated arm including reflecting mirrors arranged with respect to rotating joints to transmit the treatment laser beam to a treatment area;
   an optical relay system arranged inside the articulated arm to image the treatment laser according to scanning angles of the motorized scanners; and
   a surgical handpiece connected to the articulated arm,
   where the optical relay system comprises relay lenses arranged in multiple sets of consecutive lenses within respective light delivery pipe assemblies of the articulated arm, and the surgical handpiece does not include motorized mirror scanners.

2. The apparatus of claim 1, wherein the apparatus is configured and arranged to generate the treatment laser beam that is scanned in two axes in intermittent steps by the motorized mirror scanners, the treatment laser beam imaged through the optical relay system arranged inside the articulated arm, the treatment laser beam being focused on a spot, and the focused spot moves in two axes in intermittent steps in a surgery plane.

3. The apparatus of claim 1, wherein the apparatus is configured and arranged to generate the treatment laser beam that is scanned in two axes in continuous steps by the motorized mirror scanners, the treatment laser beam imaged through the optical relay system arranged inside the articulated arm, the treatment laser beam being focused on a spot, and the focused spot moves in two axes in continuous steps in a surgery plane.

4. The apparatus of claim 1, wherein the apparatus is configured and arranged to generate the treatment laser beam imaged through the optical relay system arranged inside the articulated arm, the treatment laser beam being focused on a spot, the focused spot moves in a surgery plane, and wherein the apparatus sensitivity to mechanical and optical misalignments is reduced by the optical relay system that is arranged in the articulated arm.

5. The apparatus of claim 4, wherein the apparatus is configured and arranged to scan the laser treatment beam in two axes in intermittent steps by the motorized mirror scanners.

6. The apparatus of claim 4, wherein the apparatus is configured and arranged to scan the laser treatment beam in two axes in continuous steps by the motorized mirror scanners.

7. The apparatus of claim 1, wherein the apparatus is configured and arranged to generate a visible aiming laser that is scanned in two axes in continuous steps by the motorized mirror scanners, the visible aiming laser imaged through the optical relay system arranged inside the articulated arm, the visible aiming laser being focused on a spot, and the focused spot moves in two axes in continuous steps in a surgery plane to form a continuous boundary outline of the treatment area.

8. The apparatus of claim 1, wherein the control device is configured and arranged to generate a two axis scanning command in response to manual movement of a computer pointing device that is connected to the apparatus.

9. The apparatus of claim 1, wherein the control device is configured and arranged to generate a two axis scanning command from a pre-programmed selection of shapes and sizes stored in a computer-readable medium.

10. The apparatus of claim 1, wherein the light delivery pipe assemblies are each fixed in length.

11. The apparatus of claim 10, wherein the treatment laser is $CO_2$ laser.

12. A laser surgical system for performing treatment by irradiating a part to be treated by a treatment laser beam, the system comprising:
- a main enclosure including a treatment laser, a visible aiming laser, and a control device;
- an articulated arm including reflecting mirrors arranged with respect to rotating joints to transmit the treatment laser beam to a treatment area;
- a compressed air spring device attached to the articulated arm to counterbalance the arm's weight; and
- an external apparatus attached to the end of the articulated arm arranged with a final focusing lens;
- wherein the main enclosure includes motorized mirror scanners controlled by the control device, the system further comprises an optical relay system arranged inside the articulated arm to image scanning angles of the motorized mirror scanners, the optical relay system comprising relay lenses arranged in multiple sets of consecutive lenses within respective light delivery pipe assemblies of the articulated arm, and the external apparatus does not include motorized mirror scanners.

13. The system of claim 12, wherein the air spring device is arranged with adjustable compressed air pressure.

14. The system of claim 12, wherein the air spring device is filled with compressed gas that is not compressed air.

15. The system of claim 12, wherein the air spring device is filled with compressed gas comprising Nitrogen.

16. The system of claim 12, wherein the air spring device is a mechanical telescopic spring device.

17. The system of claim 12, wherein the external apparatus comprises a plastic disposable hand piece comprising:
- an optical wedge to bend the treatment laser beam between five to thirty five degrees;
- the final focusing lens where the image of the scanning pivot point is in the center of the final focusing lens or in a close proximity to the center of the final focusing lens; and
- a thin metal reflector that is mounted in the disposable hand piece;
- where the optical wedge, the final focusing lens and the thin metal reflector are arranged relative to each other within the plastic disposable hand piece such that the treatment laser beam first passes through the optical wedge, then passes through the final focusing lens, and finally reflects off the thin metal reflector before exiting the plastic disposable hand piece.

18. The system of claim 17, wherein the plastic disposable hand piece is configured for use inside a human oral cavity.

19. The system of claim 17, wherein the light delivery pipe assemblies are each fixed in length.

* * * * *